(12) United States Patent
Yamanari (10) Patent No.: US 9,918,623 B2
(45) Date of Patent: Mar. 20, 2018

(54) OPTICAL TOMOGRAPHIC IMAGING APPARATUS

(71) Applicant: Tomey Corporation, Nagoya-shi (JP)

(72) Inventor: Masahiro Yamanari, Nagoya (JP)

(73) Assignee: Tomey Corporation, Nagoya-Shi (JP)

( * ) Notice: Subject to any disclaimer, the term of this patent is extended or adjusted under 35 U.S.C. 154(b) by 14 days.

(21) Appl. No.: 14/926,790

(22) Filed: Oct. 29, 2015

(65) Prior Publication Data

US 2016/0120401 A1    May 5, 2016

(30) Foreign Application Priority Data

Oct. 30, 2014    (JP) .................................. 2014-220901

(51) Int. Cl.
*G06K 9/00* (2006.01)
*A61B 3/00* (2006.01)
(Continued)

(52) U.S. Cl.
CPC ............ *A61B 3/0025* (2013.01); *A61B 3/102* (2013.01); *A61B 3/1225* (2013.01);
(Continued)

(58) Field of Classification Search
CPC ..... A61B 5/0066; A61B 5/7257; A61B 3/102; A61B 3/0025; A61B 5/0033;
(Continued)

(56) References Cited

U.S. PATENT DOCUMENTS

| 2004/0071363 A1* | 4/2004 | Kouri ................. G06K 9/00516 382/276 |
| 2006/0058592 A1* | 3/2006 | Bouma ................ A61B 5/0059 600/301 |

(Continued)

FOREIGN PATENT DOCUMENTS

JP    4344829    7/2009

OTHER PUBLICATIONS

Li et al., Coherent signal composition and global phase determination in signal multiplexed polarization sensitive optical coherence tomography, Sep. 8, 2014, vol. 22, No. 18, Optics Express, pp. 21382-21392.*

(Continued)

*Primary Examiner* — Vu Le
*Assistant Examiner* — Guillermo Rivera-Martinez
(74) *Attorney, Agent, or Firm* — Jeffrey D. Myers; Peacock Law P.C.

(57) ABSTRACT

An optical tomographic imaging apparatus capable of acquiring a two-dimensional or/and three-dimensional tomographic image having higher SNR and quality by cancelling phase change caused by birefringence of a sample in average processing using a predetermined kernel region, and calculating a global phase difference of each pixel in the kernel. The optical tomographic imaging apparatus includes a processing unit configured to: set a predetermined kernel to a B scan image or/and C scan image (volume data) acquired corresponding to a Jones matrix; model the Jones (Continued)

matrix of each pixel in the set predetermined kernel by using one or more unitary matrices to calculate a relative global phase of each pixel; and cancel the calculated relative global phase in each pixel in the predetermined kernel to average each element of the Jones matrix in the predetermined kernel.

13 Claims, 6 Drawing Sheets

(51) Int. Cl.
  *G01B 9/02* (2006.01)
  *A61B 3/10* (2006.01)
  *A61B 3/12* (2006.01)
(52) U.S. Cl.
  CPC ...... *G01B 9/02004* (2013.01); *G01B 9/02011* (2013.01); *G01B 9/02027* (2013.01); *G01B 9/02082* (2013.01); *G01B 9/02083* (2013.01); *G01B 9/02091* (2013.01); *G01B 2290/45* (2013.01); *G01B 2290/70* (2013.01)
(58) Field of Classification Search
  CPC ...... A61B 2576/00; G06T 2207/10101; G06T 2207/30004; G06T 7/0012
  See application file for complete search history.

(56) References Cited

U.S. PATENT DOCUMENTS

| | | | | |
|---|---|---|---|---|
| 2012/0099113 | A1* | 4/2012 | de Boer | A61B 5/0066 356/491 |
| 2012/0274896 | A1* | 11/2012 | Vermeer | A61B 3/102 351/205 |
| 2013/0185023 | A1* | 7/2013 | Vakoc | A61B 3/102 702/189 |
| 2016/0305762 | A1* | 10/2016 | Suter | A61B 1/00165 |

OTHER PUBLICATIONS

Ju et al., Advanced multi-contrast Jones matrix optical coherence tomography for Doppler and polarization sensitive imaging, Aug. 12, 2013, vol. 21, No. 16, Optics Express, pp. 19412-19436.*

AAPA, Lim et al., Birefringence measurement of cornea and anterior segment by office-based polarizationsensitive optical coherence tomography, Aug. 1, 2011, vol. 2, No. 8, Biomedical Optics Express, pp. 2392-2102.*

Lim, et al., "Birefringence measurement of cornea and anterior segment by office-based polarization-sensitive optical coherence tomography", Biomedical Optics Express, Jul. 27, 2011, 2392-2402.

Lu, et al., "Absolute fast axis determination using non-polarization-maintaining fiber-based polarization-sensitive optical coherence tomograph", Optics Letters, vol. 37, No. 11, Optical Society of America, Jun. 1, 2012, 1931-1933.

Park, et al., "Jones matrix analysis for a polarization-sensitive optical coherence tomography system suing fiber-optic components", Optics Letters, vol. 29, No. 21, Optical Society of America, Nov. 1, 2004, 2512-2514.

Yamanari, et al., "Fiber-based polarization-sensitive OCT for birefrigence imaging of the anterior eye segment", Biomedical Optics Express, vol. 6, No. 2, Jan. 8, 2015.

* cited by examiner

$$K_{(n)} := e^{i\Phi(n)} U_{out} \begin{bmatrix} e^{i\frac{\Delta\Phi(n)}{2}} \lambda_1 & 0 \\ 0 & e^{-i\frac{\Delta\Phi(n)}{2}} \lambda_2 \end{bmatrix} U_{in},$$

Expression (1)

$\Phi(n)$: global phase of n-th pixel in kernel $\Delta\varphi(n)$: relative phase delay between phase delay caused by birefringence of reference pixel and phase delay caused by birefringence of n-th pixel in kernel $U_{in}$, $U_{out}$: unitary matrix $\lambda_1, \lambda_2$: characteristic value of Jones matrix Js of sample at reference pixel (n=0) in kernel having unit absolute value of $|\lambda_1| = |\lambda_2| = 1$

FIG. 6A

$$\arg\{K_{H1(n)}K_{H1(0)}^* + K_{V1(n)}K_{V1(0)}^* + K_{H2(n)}K_{H2(0)}^* + K_{V2(n)}K_{V2(0)}^*\} = \Phi_{(n)} - \Phi_{(0)},$$ Expression (2)

where, $K(n) = [K_{H1(n)}, K_{H2(n)}, K_{V1(n)}, K_{V2(n)}]$.

FIG. 6B

OPTICAL TOMOGRAPHIC IMAGING APPARATUS

CROSS-REFERENCE TO RELATED APPLICATIONS

This application claims priority to and the benefit of the filing of Japanese Patent Application No. 2014-220901, filed on Oct. 30, 2014, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Field of the Invention (Technical Field)

The present invention relates to an optical tomographic imaging apparatus, and in particular, to an optical tomographic imaging apparatus that takes a tomographic image according to OCT used in ophthalmological treatment.

Description of Related Art

Because of noninvasive and contactless characteristics, the optical coherence tomography (OCT) has been widely used as a means for acquiring high-resolution tomographic images of living tissues in the department of ophthalmology.

The optical coherence tomography (OCT) is classified into time domain OCT called as a time domain method that acquires a tomographic image while moving a mirror to mechanically change an optical path length of reference beam, spectrum domain OCT called as Fourier domain method that detects spectrum information with a spectroscope to acquire a tomographic image, and optical frequency sweep OCT that detects a spectrum interference signal using a wavelength scanning light source to acquire a tomographic image.

Birefringence that changes polarization state occurs in tissues in which molecules are arrayed in a certain direction. In the retina on the fundus oculi, retina nerve fiber layer, pigmented layer of retina, vessel wall, sclera, cribrosa lamina have strong birefringence. The polarization sensitive OCT (PS-OCT) as one type of the functional OCT can visualize these tissues through tomography using birefringence. Thus, various polarization sensitive OCTs have been recently developed.

The polarization sensitive OCT (PS-OCT) uses circularly polarized light or polarization-modulated light as a measuring beam for observing a sample, and detects coherence light as two orthogonal linear polarized beams.

Japanese Patent No. 4344829 discloses an example of the polarization sensitive OCT (PS-OCT). According to this literature, simultaneously with (in synchronization with) B scan, a polarized beam from a light source (beam linearly polarized by a polarizer) is continuously modulated using an EO modulator (polarization modulator, electro-optic modulator). The continuously modulated polarized beam is divided, one beam is projected to a sample to acquire reflected light, and the other beam is used as reference beam. In OCT measurement based on spectrum interference of the beams, out of the spectrum interference components, a vertical polarization component and a horizontal polarization component are simultaneously measured using two optical detectors to obtain a Jones matrix indicating polarization characteristics of the sample.

According to a method disclosed in Lim et al., "Birefringence measurement of cornea and anterior segment by office-based polarization-sensitive optical coherence tomography"BIOMEDICAL OPTICS EXPRESS, Vol. 2, No. 8, Aug. 1, 2011, 2392, to improve the SNR (signal noise ratio) and quality of the image corresponding to the Jones matrix obtained by use of the polarization sensitive OCT (PS-OCT), a B scan image corresponding to the Jones matrix is subjected to moving average processing, for example, with a kernel size of 3×5 pixels.

When the B scan image corresponding to the Jones matrix is subjected to the moving average processing with a predetermined kernel size as in Lim et al., to reduce speckle noise, the method of finding a global phase difference of each pixel in the kernel and cancelling the global phase difference has been proposed.

However, since phase change caused by birefringence of a test sample (hereinafter referred to as "sample") cannot be distinguished from global phase, the birefringence of the sample may become an artifact for the global phase.

To solve the above-mentioned problem, an object of the present invention is to provide an optical tomographic imaging apparatus for acquiring a two-dimensional or/and three-dimensional tomographic image corresponding to a Jones matrix acquired by a polarization sensitive OCT (PS-OCT), the apparatus performing average processing using a predetermined kernel region, in which a phase change caused by birefringence of a sample is cancelled to calculate a global phase difference of each pixel in the kernel, to perform moving average processing, thereby acquiring a two-dimensional or/and three-dimensional tomographic image having higher SNR and quality.

BRIEF SUMMARY OF THE INVENTION

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

To attain the above-mentioned object, the present invention provides a polarization sensitive OCT (PS-OCT) apparatus for acquiring Jones matrix representing polarization characteristics of a sample (object to be inspected). The apparatus includes a processing unit configured to: set a predetermined kernel to OCT data that are associated with polarimetric properties of the object, defined in spatial and/or temporal directions (for example, pixel scope in XZ direction or/and XYZ direction); model the Jones matrix of each pixel in the set predetermined kernel by using one or more unitary matrices to calculate a relative global phase of each pixel; and cancel the calculated relative global phase in each pixel in the predetermined kernel to average each element of the Jones matrix in the predetermined kernel.

Figure 6A:
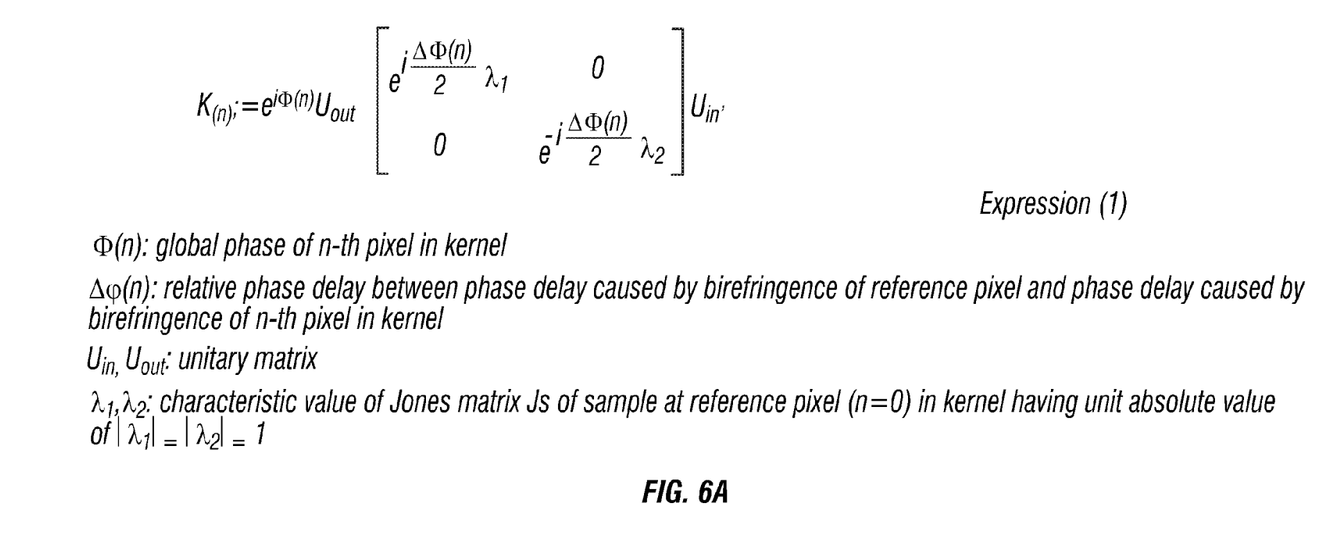
Figs. 6A and 6B illustrate expressions for calculating a relative global phase in each pixel according to the present invention.
Figure 6B:
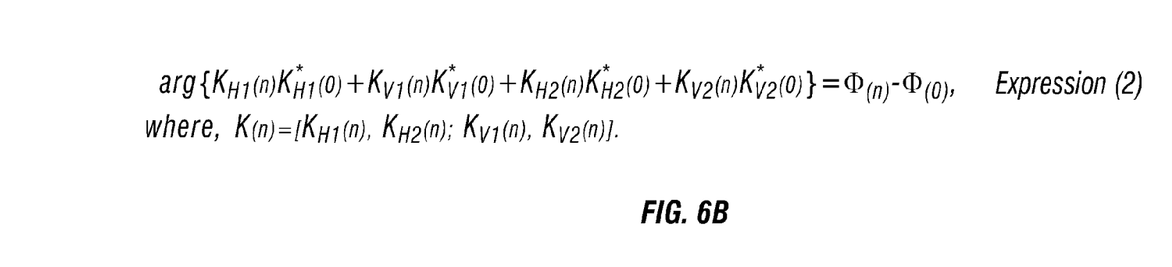

By modelling the Jones matrix in each pixel in the predetermined kernel by use of global phase of each pixel and unitary matrices Uin, Uout according to an expression (1) in FIG. 6, and parameterizing elements of unitary matrices Uin, Uout to calculate a relative global phase $\varphi(n)-\varphi(0)$ with respect to a reference pixel (n=0) according to an expression (2) in FIG. 6, a relative phase delay between reference pixel and each pixel due to birefringence is cancelled, and a relative global phase without any artifact of birefringence of the sample is calculated. Therefore, the global phase of each pixel in the predetermined kernel can be effectively cancelled.

To attain the above-mentioned object, according to a first aspect of the present invention, in the optical tomographic imaging apparatus, the pixel having the highest S/N ratio in the predetermined kernel is detected as a reference pixel, and the relative global phase of each pixel is calculated with respect to the global phase of the detected reference pixel.

By setting the pixel having the highest S/N ration in the predetermined kernel as the reference pixel, the global phase can be cancelled more effectively.

To attain the above-mentioned object, according to a first or second aspect of the present invention, in the optical tomographic imaging apparatus, each element (pixel value) of Jones matrix of each pixel in the predetermined kernel in X direction or/and Y direction or/and Z direction is subjected to predetermined weighting processing.

Figure 5:
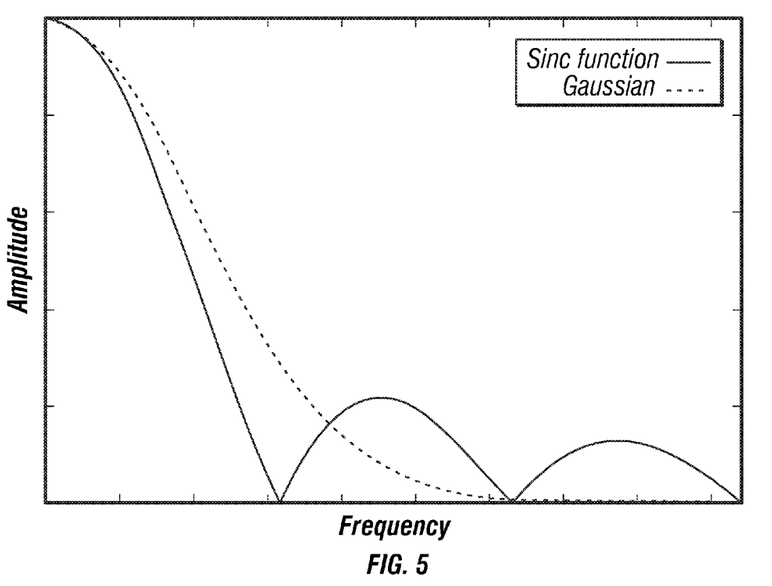
FIG. 5 illustrates spatial frequency characteristics of an SINC function (solid line) and Gaussian function (dotted line) in Fourier space.

For example, when the kernel is two-dimensional, Gaussian waveform processing of 0 to 1 in the X direction and the Z direction is executed for averaging. Since executing the Gaussian waveform processing in real space is equivalent to multiplying a Fourier transformed measurement signal by a Gaussian function in Fourier space as shown in FIG. 5 with dotted line, high-frequency noise can be spatially removed with efficiency. The average processing can be executed more effectively by executing weighting processing in this manner.

According to the present invention, since the phase shift caused by birefringence of the sample can be cancelled by using the expressions (1) and (2) in FIG. 6 to calculate the relative global phase of each pixel in the kernel, the global phase of each pixel can be effectively cancelled in averaging processing to acquire a two-dimensional or/and three-dimensional tomographic image having higher SNR and quality.

Figure 1:
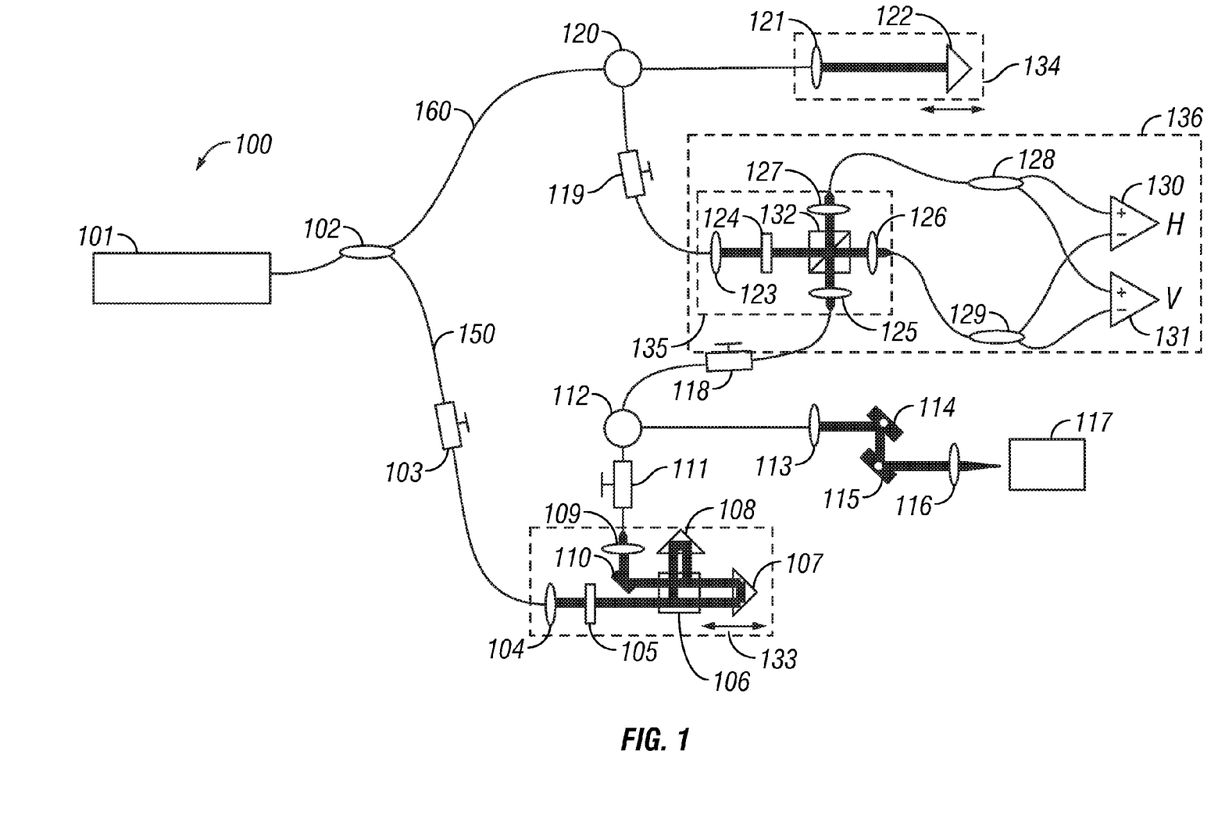
FIG. 1 is a view illustrating an example of an optical tomographic image acquisition section according to the present invention in detail.

An optical tomographic imaging apparatus in accordance with an embodiment of the present invention will be described below with reference to figures. FIG. 1 illustrates detailed configuration of a tomographic image acquisition section 100.

As illustrated in FIG. 1, in the tomographic image acquisition section 100, a sample (object to be inspected) 117 is irradiated with a measuring beam to take a two-dimensional or/and three-dimensional tomographic image of the sample 117. This embodiment adopts a Fourier domain (optical frequency sweep) method using a wavelength scanning light source 101 that changes wavelength with time during scanning.

That is, light output from the wavelength scanning light source 101 is input to a fiber coupler 102 though an optical fiber. The fiber coupler 102 divides the light into a reference beam and a measuring beam with a ratio of 5:95, for example, and outputs the reference beam and the measuring beam to a reference arm 160 and a sample arm 150, respectively. The reference beam output to the reference arm 160 is input to an optical circulator 120 through the optical fiber and then, is input to a collimator lens 121, and is incident onto a reference mirror 122. To adjust the optical path length difference between the reference and sample arms, the reference mirror 122 can be moved on the optical path axis. Prior to measurement of an OCT tomographic image, a measurement optical path length is aligned with a reference optical path length.

Then, the reference beam reflected on the reference mirror 122 travels from the collimator lens 121 to the optical circulator 120 through the optical fiber, changes its optical path there, passes through a polarization controller 119, and is input to a collimator lens 123 and to a polarization sensitive detection arm 136.

Meanwhile, the measuring beam output from the fiber coupler 102 to a sample arm 150 is input to a collimator lens 104 of a polarization-dependent delay line 133 through an optical fiber and a polarization controller 103, and then passes through a polarizer 105. In this embodiment, the polarization angle of the polarizer 105 is set to 45 degrees. The polarization angle of the beam that passes through the polarization controller 103 and is about to enter the collimator lens 104 is also set to 45 degrees, and the polarization controller 103 and the polarizer 105 are adjusted and controlled so as to efficiently take out the measuring beam polarized by 45 degrees.

The measuring beam polarized by 45 degrees is divided into two linearly polarized (vertical and horizontal) beams orthogonal to each other through a polarized beam splitter 106 in the polarization-dependent delay line 133. The divided measuring beams are reflected on different total reflection prisms 107 and 108 respectively, and propagate in two different optical paths. The movement of at least one of the total reflection prisms 107 and 108 is controlled, generating a delay between the two differently polarized (vertical and horizontal) beams.

Here, by setting the incident measuring beam so as to be incident onto the position away from the center of the polarized beam splitter 106 by a certain distance, two differently polarized beams are generated by the polarized beam splitter 106. The beams are reflected on the respective total reflection prisms 107 and 108 to generate two differently polarized (vertical and horizontal) measuring beams with a certain delay. The measuring beam changes its optical path at a reflection mirror 110 and then, is connected to an optical fiber through a collimator lens 109.

The measuring beam passes through a polarization controller 111 via the optical fiber, changes its optical path at an optical circulator 112, is incident onto a collimator lens 113, is reflected on galvanometer mirrors 114 and 115, is concentrated at a lens 116, and is incident onto the sample 117.

The galvanometer mirrors 114 and 115 function to cause the measuring beam to scan the sample. The galvanometer mirrors 114 and 115 are controlled to cause the measuring beam to scan the surface of the sample 117 in the horizontal and vertical directions. This can acquire a two-dimensional tomographic image or a three-dimensional tomographic image of the sample 117.

The measuring beam reflected on the sample 117 passes the lens 116, and the galvanometer mirrors 115 and 114 in the reverse order, and is input to the collimator lens 113. Then, the measuring beam passes through the optical fiber, changes its optical path at the optical circulator 112, and then, passes through a polarization controller 118, and is input to a collimator lens 125 and to the polarization-sensitive detection arm 136.

The reference beam that is input from the collimator lens 123 to the polarization-sensitive detection arm 136 and is polarized at the polarizer 124 and the measuring beam reflected on the sample 117 are combined and divided using a nonpolarized beam splitter 132. After that, the divided beams are input to collimator lenses 126 and 127, and are divided into two orthogonal polarized beams by two in-line polarized beam splitters 128 and 129.

To equalize power of the linear polarized beams in the vertical and horizontal directions that have passed the in-line polarized beam splitters 128 and 129, the polarization angle of the polarizer 124 is adjusted to 45 degrees. Here, to improve efficiency, the polarization angle of the beam that is about to enter the polarizer 124 is controlled to be 45 degrees by using the polarization controller 119 in advance.

Figure 2:
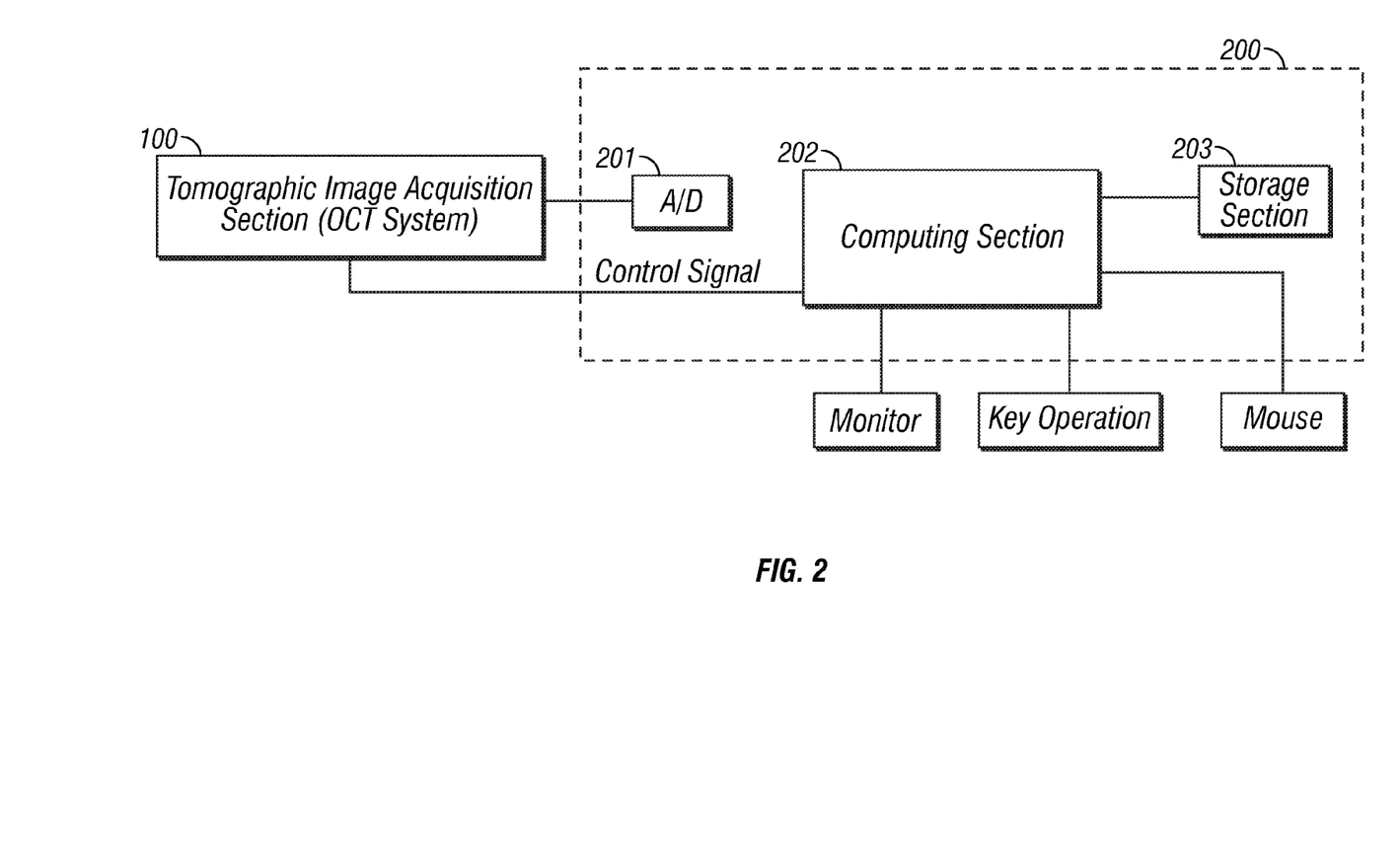
FIG. 2 is a view illustrating configuration of an optical tomographic imaging apparatus.

The interference of two polarization states is detected with two balance optical detectors 130 and 131. Two interference signals that one has the vertical polarized state and another has horizontal polarized state are subjected to processing such as Fourier transform at a computing section 202 of a controller 200 illustrated in FIG. 2 to acquire a B scan image or/and C scan image (volume data) corresponding to a Jones matrix of the sample 117. The acquired tomographic image is stored in a storage section 203.

Figure 4A:
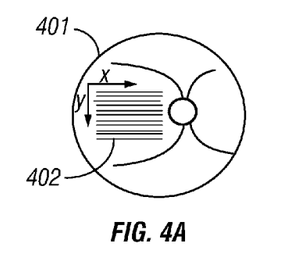
FIGS. 4A, 4B, and 4C illustrate an acquisition flow of a three-dimensional tomographic image.
Figure 4B:
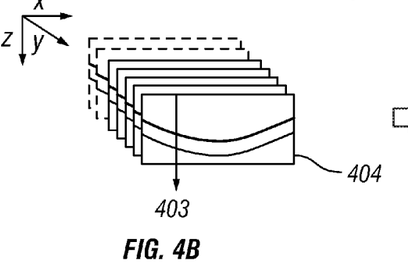
Figure 4C:
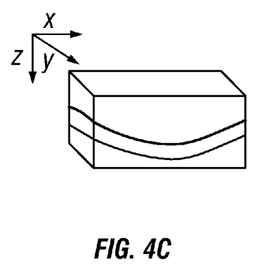

FIGS. 4(a)-4(c) illustrate how to acquire a tomographic image (B scan image) at the tomographic image acquisition section 100. FIG. 4(a) illustrates an example of a fundus oculi retina of an eye E to be inspected, and FIG. 4(b) illustrates a plurality of two-dimensional tomographic images (B scan images) of the fundus oculi retina 401, which are acquired at the tomographic image acquisition section 100. FIG. 4(c) illustrates an example of a C scan image (three-dimensional tomographic image, also referred to as volume data) of the fundus oculi, which is generated in this embodiment. An x axis in FIGS. 4(a) to 4(c) represents a B scan direction, and y axis represents a C scan direction. A z axis in FIGS. 4(b) and 4(c) represents a depth direction of an A scan signal, that is, a depth direction of the fundus oculi.

A two-dimensional tomographic image 404 in FIG. 4(b) is generated by recreating the A scan signal 403 at the computing section 202 while allowing a galvanometer mirror unit 106 to scan in an X direction. The two-dimensional tomographic image is a B scan image that is a two-dimensional tomographic image on the two-dimensional cross section in the X direction orthogonal to the depth direction (Z direction) of the fundus oculi retina 401, that is, the plane defined by the x axis and the z axis in FIG. 4(b). A reference numeral 402 in FIG. 4(a) represents the position where the two-dimensional tomographic image 404 is taken.

The B scan image and the C scan image in FIG. 4 each are configured of a plurality of pixels. According to the present invention, in the moving average, for example, in the case of the B scan image (two-dimensional image), a region having a predetermined number of pixels in the X direction and the Z direction (for example, in the case of 3 pixels in the X direction and five pixels in the Z direction, a region of 3×5 pixels) is defined as a predetermined kernel region. In the moving average for the C scan image, a region having a predetermined number of pixels in the X direction, the Y direction, and the Z direction is defined as the predetermined kernel region.

Figure 3:
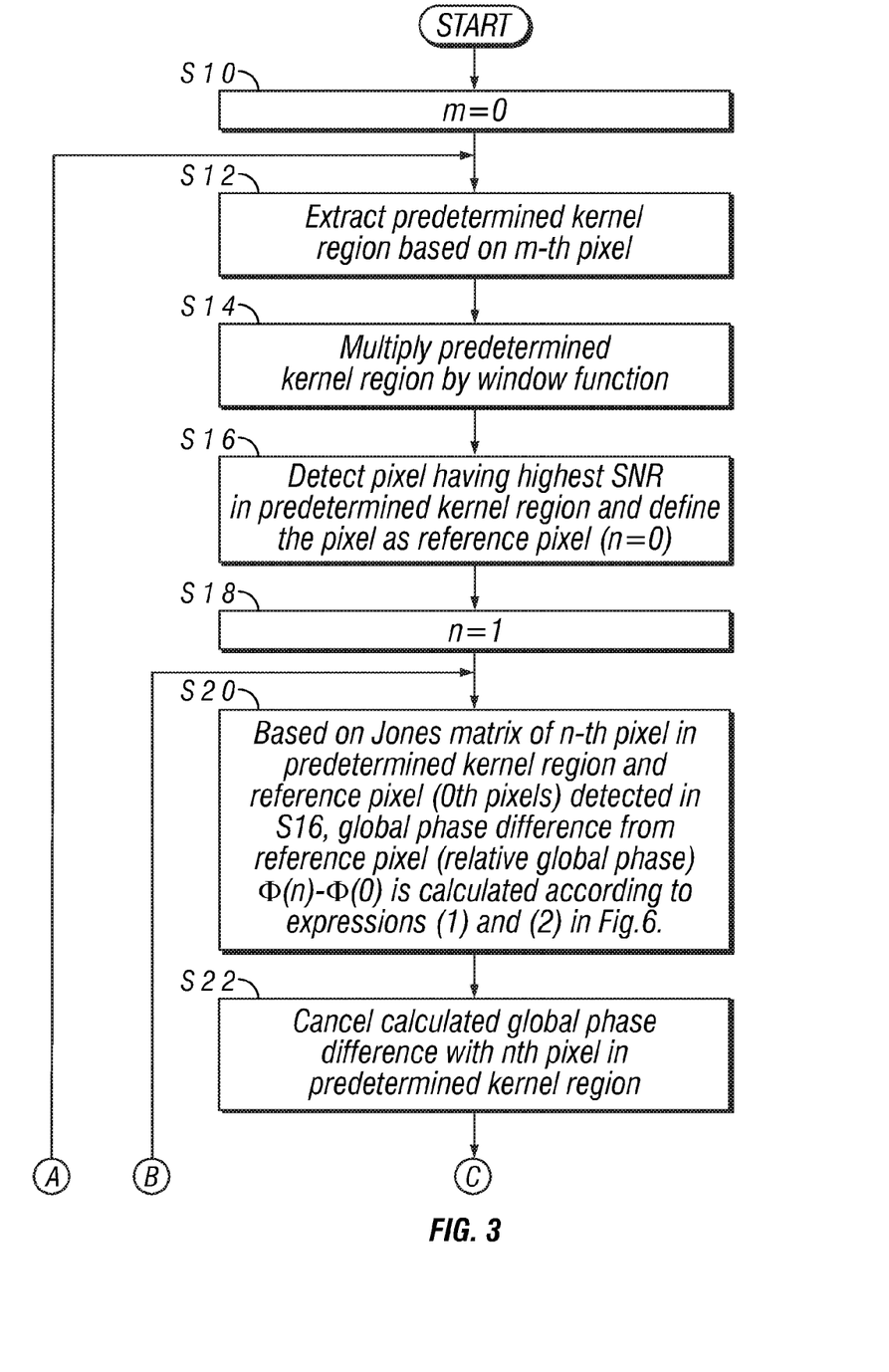
FIG. 3 is a flow chart of moving average processing.

Next, moving average processing of the acquired image, which is a subject matter of the present invention, will be described below with reference to a flow chart in FIG. 3.

To improve the SNR (signal noise ratio) and quality, the acquired image is subjected to the moving average processing. A flow illustrated in FIG. 3 is an example of the moving average processing, and the moving average processing is not limited to this flow.

First, in S10, a first pixel is set. The first pixel is a 0th pixel and thus, in S10, m is set to 0, and the set pixel is defined as m-th pixel.

In S12, a predetermined kernel region is extracted from volume data stored in the storage section 203 on the basis of the m-th pixel. For example, when one B scan image is subjected to the moving average processing, a region having a predetermined number of pixels in the X direction and the Z direction including the m-th pixel (described as "kernel region" according to the present invention, for example, 3 pixels×5 pixels) is extracted. The positional relationship between the kernel region and the m-th pixel may be previously set. A uniform relationship facilitates the extraction, achieving the higher effect of the moving averaging processing.

When the volume data is subjected to the moving average processing, the kernel region of a predetermined number of pixels in the X direction, the Y direction, and the Z direction including the m-th pixel (ex. 3×5×3 pixels) is extracted.

In S14, the extracted kernel region is multiplied by a window function. In the case of the B scan image, the function may be multiplied in the X direction and the Z direction, and in the case of the volume data, the function may be multiplied in the X, Y, and Z directions. When applicable, one of the X, Y, and Z directions may be selected, and two of the X, Y, and Z directions may be selected in the case of the volume data.

Gaussian function (also referred to as Gaussian window) may be used as the window function. Due to a spatial frequency characteristic represented by a dotted line in FIG. 5, Gaussian function enables efficient removal of noise at high frequencies.

In S14, each element of Jones matrix of each pixel is multiplied by the window function such as Gaussian function. The window function is not limited to Gaussian function, and may be Hamming function (also referred to as Hamming window) or Hanning function (also referred to as Hanning window). Also with these functions, the same effect as Gaussian function can be obtained.

After the kernel region is multiplied by the window function in S14, in S16, the SNR (signal noise ratio) of each pixel in the kernel region is calculated to detect the pixel having the highest SNR, and the detected pixel is defined as a reference pixel (n=0).

In S18, n is set to 1, and an nth pixel other than the reference pixel is detected.

In S20, based on the Jones matrix of the nth pixel in the detected predetermined kernel region and the reference pixel (0th pixels) detected in S16, a global phase difference from the reference pixel (relative global phase) $\varphi(n)-\varphi(0)$ is calculated according to the expressions (1) and (2) in FIG. 6.

FIG. 6 illustrates mathematical expressions for calculating the relative global phase in each pixel according to the present invention. The expression (1) is an expression of modelling the Jones matrix of the n-th pixel in kernel by using the global phase and unitary matrices Uin, Uout. Details of each parameter are as described in FIG. 6.

Then, elements of the unitary matrices Uin, Uout are parameterized, and the relative global phase $\varphi(n)-\varphi(0)$ with respect to the reference pixel can be derived according to the expression (2) in FIG. 6. The global phase difference (relative global phase) $\varphi(n)-\varphi(0)$ from the reference pixel is calculated by using the expression (2). Since the expression (2) has no $\Delta\varphi(n)$, $\lambda 1$, $\lambda 2$ and Uin, Uout, the relative global phase $\varphi(n)-\varphi(0)$ without any artifact due to birefringence of the sample can be calculated using the expression (2). The relative global phase is calculated for each element of the Jones matrix of the pixels.

In S22, using the global phase difference of each element of the Jones matrix of the n-th pixel in the predetermined kernel region, which is calculated in S20, the global phase difference of each element of the Jones matrix of the n-th pixel is cancelled. The global phase difference of the n-th pixel in the kernel region is cancelled in this manner.

After the global phase difference of n-th pixel is cancelled in S22, in S24, 1 is added to n, and the processing in S20 to S22 is performed on the next pixel in the predetermined kernel region to cancel the global phase difference (relative global phase) in the same manner.

When the relative global phase of all pixels in the predetermined kernel region is cancelled in S26 (n>n (Final)), values for each element of the Jones matrix of each pixel in the predetermined kernel region are averaged in S28.

When the values for each element of the Jones matrix are averaged in S28, 1 is added to the number of pixel in S30. When the value the added value of m is larger than a predetermined number m (final) in S32, it is determined that the moving average processing is completed in the entire scope of the target B scan image or volume data to finish the moving average processing. When the added value of m is the predetermined number m (final) or less, the procedure returns to S12, the kernel region of the next pixel is extracted, and the processing in S12 to S28 is repeated.

The predetermined number m (final) in S32 may be a total number of pixels of the target B scan image or volume data. In this case, the target B scan image or volume data is subjected to the moving average processing over the entire region. The predetermined number m is not limited to the total number of pixels, and may be a predetermined smaller number. For example, when it is attempted to check any characteristic site of the B scan image or volume data, the value of m (final) corresponding to the characteristic site may be set.

As described above, since the phase shift caused by birefringence of the sample is cancelled by using the expressions (1) and (2) in FIG. 6 to calculate the relative global phase of each pixel, the relative global phase can be calculated more accurately. This results in more effective averaging processing to acquire a two-dimensional or/and three-dimensional tomographic image having higher SNR and quality.

Since the expression (2) in FIG. 6 is an expression of calculating a signal phase difference between two pixels (0th pixel and the n-th pixel) in the predetermined kernel region, the signal phase difference between different A scan images at any depth can be found according to the expression (2). That is, since Doppler phase shift, with the phase shift caused by birefringence of the sample cancelled, can be calculated by using the expression (2), the expression (2) can be also applied to Doppler OCT. In addition, since a phase difference between an OCT signal before and after added stress to the sample can be calculated by using the expression (2), the expression (2) can be also applied to OCT elastography.

Although the embodiment of the present invention has been described in detail, the embodiment is merely an example. The present invention should not be limited by specific description in such embodiment, but may be changed, modified, or improved, and implemented in any manner by those skilled in the art. Further, it should be appreciated that such modifications fall within the scope of the present invention so as not to deviate from the subject matter of the present invention.

According to the present invention, the expressions (1) and (2) for calculating the relative global phase of each pixel are disclosed in FIG. 6. However, the expression for calculating the relative global phase is not limited to the expressions (1) and (2), and the expression may be partially changed or include additional parameters.

REFERENCE SIGNS LIST

100: tomographic image acquisition section
101: wavelength scanning light source
102: fiber coupler
106: polarized beam splitter
112, 120: optical circulator
128, 129: in-line polarized beam splitter
130, 131: balance optical detector
132: nonpolarized beam splitter
133: polarization-dependent delay line
201: AD board
202: computing section
203: storage section Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An optical tomographic imaging apparatus that is a polarization sensitive optical coherence tomography (OCT) (PS-OCT) for acquiring a Jones matrix representing polarization characteristics of at least one object to be inspected, the apparatus comprising at least one processing unit configured to:

set a predetermined kernel of adjacent pixels to acquire OCT data that are associated with polarimetric properties of the object, defined in spatial and/or temporal directions;

define one of the pixels as a reference pixel: and model the Jones matrix of each pixel in the set predetermined kernel by using one or more unitary matrices to obtain a relative global phase of each pixel between the reference pixel and each pixel without any artifact of birefringence.

2. The optical tomographic imaging apparatus according to claim 1, wherein the pixel having the highest S/N ratio in the predetermined kernel is detected as a reference pixel, and the relative global phase of each pixel is calculated with respect to the global phase of the detected reference pixel.

3. The optical tomographic imaging apparatus according to claim 1, wherein each element (pixel value) of Jones matrix of each pixel in the set predetermined kernel in X direction or/and Y direction or/and Z direction is subjected to predetermined weighting processing.

4. The optical tomographic imaging apparatus according to claim 3, wherein the predetermined weighting processing is Gaussian processing.

5. The optical tomographic imaging apparatus according to claim 3, wherein the predetermined weighting processing is window function processing.

6. The optical tomographic imaging apparatus according to claim 2, wherein each element (pixel value) of Jones matrix of each pixel in the set predetermined kernel in X direction or/and Y direction or/and Z direction is subjected to predetermined weighting processing.

7. The optical tomographic imaging apparatus according to claim 6, wherein the predetermined weighting processing is Gaussian processing.

8. The optical tomographic imaging apparatus according to claim 6, wherein the predetermined weighting processing is window function processing.

9. The optical tomographic imaging apparatus according to claim 1, wherein the relative global phases in the predetermined kernel are cancelled to estimate a Jones matrix in the predetermined kernel.

10. The optical tomographic imaging apparatus according to claim 1, wherein the relative global phase is used to estimate the local displacement of the object.

11. The optical tomographic imaging apparatus according to claim 5, wherein the window function processing is one or both of Hamming and Hanning.

12. The optical tomographic imaging apparatus according to claim 8, wherein the window function processing is one or both of Hamming and Hanning.

13. The optical tomographic imaging apparatus according to claim 10, wherein the apparatus is used for an application selected from the group consisting of Doppler optical coherence tomography (OCT), and OCT elastography.

* * * * *